(12) United States Patent
Horn et al.

(10) Patent No.: US 12,106,494 B2
(45) Date of Patent: Oct. 1, 2024

(54) METHOD AND DEVICE FOR REGISTERING TWO MEDICAL IMAGE DATA SETS TAKING INTO ACCOUNT SCENE CHANGES

(71) Applicant: Ziehm Imaging GmbH, Nuremberg (DE)

(72) Inventors: Andreas Horn, Stein (DE); Thomas König, Nuremberg (DE); Christof Fleischmann, Möhrendorf (DE)

(73) Assignee: Ziehm Imaging GmbH, Nuremberg (DE)

( * ) Notice: Subject to any disclaimer, the term of this patent is extended or adjusted under 35 U.S.C. 154(b) by 458 days.

(21) Appl. No.: 17/647,317

(22) Filed: Jan. 6, 2022

(65) Prior Publication Data
US 2022/0270270 A1    Aug. 25, 2022

(30) Foreign Application Priority Data
Feb. 25, 2021   (DE) ...................... 10 2021 001 022.1

(51) Int. Cl.
| | |
|---|---|
| *G06T 7/00* | (2017.01) |
| *A61B 6/00* | (2024.01) |
| *G06T 7/10* | (2017.01) |
| *G06T 7/30* | (2017.01) |

(52) U.S. Cl.
CPC .............. *G06T 7/30* (2017.01); *A61B 6/4441* (2013.01); *A61B 6/5211* (2013.01); *G06T 7/0012* (2013.01); *G06T 7/10* (2017.01); *G06T 2207/10028* (2013.01); *G06T 2207/10116* (2013.01)

(58) Field of Classification Search
None
See application file for complete search history.

(56) References Cited

U.S. PATENT DOCUMENTS

| | | | |
|---|---|---|---|
| 7,596,283 B2 | 9/2009 | Xu et al. | |
| 8,605,964 B2 * | 12/2013 | Fichtinger | A61N 5/1027 382/128 |
| 2010/0061611 A1 * | 3/2010 | Xu | G06T 7/337 378/4 |
| 2012/0289825 A1 * | 11/2012 | Rai | A61B 6/547 600/425 |
| 2014/0073907 A1 * | 3/2014 | Kumar | A61B 10/0241 600/407 |

(Continued)

*Primary Examiner* — Idowu O Osifade
(74) *Attorney, Agent, or Firm* — Knobbe, Martens, Olson & Bear LLP (57) ABSTRACT

A method of registering two sets of medical image data taking into account scene changes can include providing a first and a second medical image data set by means of a medical device, subdividing the first and second medical image data sets into an equal number of sub-images, performing a number of individual registrations between the first and second medical image data sets with respective optimization of a similarity measure, identifying the sub-images that have a scene change, and performing a final registration between the first and the second medical image data set by masking out the identified sub-images or a masked out sub-image combination. For each individual registration, at least one sub-image of the first and/or second medical image data set can be masked out by means of a random process when determining the respective measure of similarity.

14 Claims, 7 Drawing Sheets

(56) References Cited

U.S. PATENT DOCUMENTS

2014/0334709 A1* 11/2014 Siewerdsen .............. G06T 7/32
                                                    382/132
2016/0171698 A1*  6/2016 Razeto .................... G06T 7/149
                                                    382/128

* cited by examiner

METHOD AND DEVICE FOR REGISTERING TWO MEDICAL IMAGE DATA SETS TAKING INTO ACCOUNT SCENE CHANGES

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

The present disclosure generally relates to the field of intraoperative imaging, and more specifically to registration of multiple medical image data sets.

Description of the Related Art

Registration is a method of image processing in which a coordinate transformation or association is determined between at least two images, such that a mutual association of the image contents can be established. Generally, this association may be calculated between two images which were recorded at different times, by means of different imaging methods, and/or under different recording conditions.

It proves to be of particular complexity when registering between two images if portions of one of the two images differ considerably from corresponding portions of the respective other image, for example by the presence of foreign objects which can cover parts of image areas and/or by the occurrence of movement of a medical area to be examined. The presence of such a case, referred to herein as a scene change, can considerably influence the value of a similarity measure between the images. The result can be that a correct coordinate transformation cannot be calculated between the images, or that it is unusable. Particularly in the field of medical imaging, it is desirable to avoid such cases from a risk point of view.

For the mutual registration of two images, there are various aspects which can be taken into account, for example if the images to be registered originate from different image recording devices or if they were produced using different imaging methods. In this case, image contents can already differ due to different exposure methods. For example, in X-ray imaging, these can be, for example, an X-ray C-arm (C-arm), for example also a mobile X-ray C-arm and an X-ray computer tomograph (CT). The noise and contrast conditions occurring in images can likewise impair the registration method, in particular to the extent that associations between the images can be determined with insufficient required accuracy. Furthermore, the degrees of freedom available during a registration (translation, rotation, scaling, shearing, elastic/inelastic transformation) can play a role. If several degrees of freedom are available for a registration, the probability of a successful registration between two images is greater, but the number of possible degrees of freedom available for a registration scales, even with a longer (computing) time for the registration.

Document U.S. Pat. No. 7,596,283 discloses a method for registration between two image data sets, in which features extracted from an image are used, which may be suitable for elastic registrations.

SUMMARY

An example problem addressed by certain embodiments of the present technology is that of providing an improved method and an improved device for the registration of two or more medical image data sets. Without limiting the scope of the present disclosure, certain advantageous features are recited in the claims of the present application.

In a first aspect, a method of registering two sets of medical image data taking into account scene changes comprises, under control of one or more processors, a) receiving a first medical image data set and a second medical image data set from one or more medical devices; b) subdividing each of the first and second medical image data sets into an equal number of sub-images; c) performing a plurality of individual registrations between the first and second medical image data sets with respective optimization of a similarity measure, wherein, for each individual registration, at least one sub-image of the first and/or second medical image data set is masked out by means of a random process when determining the respective similarity measure; d) identifying the sub-images that have a scene change; and e) performing a final registration between the first medical image data set and the second medical image data set by masking out the sub-images identified in step d or a masked-out sub-image combination used in step c.

In some embodiments, both medical image data sets are three-dimensional volume images.

In some embodiments, the first medical image data set and the second medical image data set are each subdivided into n×m×p sub-images.

In some embodiments, both medical image data sets are two-dimensional images, preferably at least one of projection images or sectional images.

In some embodiments, the first medical image data set and the second medical image data set are each subdivided into n×m sub-images.

In some embodiments, at least two sub-images are masked out for steps d and e, and wherein completely different or only partially different sub-images are masked out for each registration of step c.

In some embodiments, when determining the respective similarity measure, the sub-images are weighted with an information content determined within the corresponding sub-images.

In some embodiments, identifying the sub-images that have a scene change comprises creating a ranking of the determined similarity measures; determining a set of best similarity measures based on the created ranking and determining the masked-out sub-images in the calculation thereof; and identifying the specific sub-images whose frequency exceeds a threshold value as the sub-images which have a scene change.

In some embodiments, the method further comprises subdividing the sub-images into sub-sub-images.

In some embodiments, the method further comprises determining a sub-similarity measure for each non-masked sub-image, wherein the determined similarity measures are aggregated from the sub-similarity measures.

In some embodiments, the at least one sub-image to be masked out is selected pseudo-randomly for each individual registration.

In a second aspect, an X-ray device comprises an image processing unit having a memory unit storing instructions that, when executed, cause one or more processors of the image processing unit to execute any of the foregoing methods.

In a third aspect, a tangible, non-transitory computer-readable storage medium has stored thereon a computer program which can be loaded directly into a memory unit of a control unit of an X-ray device, in particular a C-arm X-ray device, having program sections in order to execute any of the foregoing methods.

In a fourth aspect, a tangible, non-transitory computer-readable storage medium has stored thereon program sections which can be read and executed by a computer unit to execute any of the foregoing methods.

DETAILED DESCRIPTION

The present technology provides systems and methods suitable for registration of multiple medical image data sets. Mutual assignment of image contents between two images can be based on the use of a similarity measure. The similarity measure quantitatively describes the correspondence between two images or image regions. The similarity measure can be determined and/or maximized by means of mathematical methods, particularly by means of methods of mathematical optimization, in order to achieve the highest possible accuracy of the registration. Such a maximization of a similarity can also be understood mathematically as the minimization of a dissimilarity and can be converted to a dissimilarity by multiplication by −1, for example. Both cases will be referred to below with the term optimization and will be treated as equivalent. Such an optimization may be based on the calculation of many individual similarity measures in individual optimization steps, for example iteratively or in parallel.

A further possibility for registration is the determination of similarity measures in several small image regions, or sub-images, instead of a single similarity measure for an entire image. These similarity measures may be combined to form an overall or aggregated similarity measure according to the calculation, for example by summation. The individual similarity measures can be weighted with an information content determined within the corresponding sub-images. In this case, the information content can be determined quantitatively, for example, by the standard deviation, the variance or the entropy of the intensity or pixel values of a sub-image. This method may be particularly suitable if there are many comparatively homogeneous image regions which cannot improve or might even impair the quality of the desired registration. However, such an approach may be disadvantageous on its own if there is a scene change characterized by a particularly high information content between the two images. In the case of medical image data sets such as X-ray images, this can arise, for example, if a foreign object, such as an operating instrument or an implant, appears in only one of the two image data sets. A foreign object of this kind usually has a comparatively high contrast and thus a high information content, which leads to a concomitant high weighting in the calculation of the aggregated degree of similarity. However, if the location of the foreign object differs in the two images, or if the foreign object is present in only one of the image data sets, the result of the registration will be significantly and negatively affected.

Depending on the type of image data sets, the image data described herein may be recorded by means of a corresponding medical device. In the case of X-ray images, such medical imaging devices can be, for example, mobile or stationary X-ray C-arms, computer tomographs (CT) or other modalities from the group of X-ray-imaging medical devices. Imaging methods which are based on the principles of magnetic resonance can be, for example, magnetic resonance tomographs (MRI). The methods according to the present technology further provide for processing medical image data records which were generated by means of an ultrasonic apparatus.

First and second medical image data sets can be provided by different or the same medical imaging methods; for example, one medical image data set can be provided by a magnetic resonance tomograph, while the other image data set can be provided by an X-ray device. The methods according to the present technology also include the possibility that the medical image data sets can be recorded by means of the same recording technology, for example by means of X-rays, but the recording modalities can differ; for example, one medical image data set can be recorded by means of a CT device, while the other can be recorded by means of a C-arm. In particular, one of the image data sets to be registered can also be synthesized from an existing image data set, for example by forward projection of a synthetic, two-dimensional X-ray image from a previously obtained three-dimensional computer tomography (Digitally Reconstructed Radiograph, DRR). In this case, the other image data set can correspond to a true X-ray image which can be registered or brought into coincidence with the synthesized image as part of a 3D/2D registration. The method according to the invention can thus also be used as part of such a 3D/2D registration.

In the methods of the present technology, the two image data sets can be identical or the same for successful registration between the first and the second image data sets, so that the contents of the image data sets do not differ from one another, and consequently it is not necessary for a scene change to be present. In accordance with the methods of the present technology, a registration can also be successful if the two medical image data records differ, e.g., when a scene change is present. A scene change can be present, for example, if foreign objects are present in one of the two medical image data sets.

In the methods according to the present technology, foreign objects that may be present in one or both of the two medical image data sets may include, but are not limited to, screws, Kirschner wires, implants, clamps, tubes, instruments, scissors, scalpels or combinations thereof. According to the present technology, extraneous anatomical structures located in at least one of the two medical image data sets can also be identified as foreign objects, for example, tumors and/or hands of the surgeon during the preparation of the recording of a medical image data set. Furthermore, differences between the two medical image data sets which differ in at least one property, for example contrast, illumination, radiation dose or other image recording parameters, are also considered scene changes.

In some embodiments, the first and the second medical image data sets can each be subdivided into an equal number of sub-images (e.g., components or portions), which may in some cases be of equal size. The medical image data sets can be subdivided into any number of sub-images, but the number of sub-images of the first and second medical image data sets can be identical and of equal size. Alternatively, it is possible that individual sub-images can overlap. Alternatively, such a subdivision of the medical image data set can also be understood as a classification.

In some embodiments, a number of individual registrations, e.g., at least one registration, between the first and the second medical image data sets are performed, with a similarity measure being determined and optimized in each case. The individual registrations of the methods according to the present technology can be rigid (e.g., inelastic) registrations, but it is also possible to carry out an elastic registration. A similarity measure can be understood as a numerical value, for example, in a value range from 0 to 1, which contains information about the extent to which the images to be registered correspond to one another. A value of 0 for the similarity measure can mean that the images do not match each other in any area, for example in any sub-image. On the other hand, a value of "1" may mean that the two medical image data sets completely match, for example a match in all the sub-images.

For each individual registration, at least one sub-image of the first medical image data set, and preferably a corresponding sub-image of the second medical image data set, may be masked out by means of a random process, e.g., a stochastic or nondeterministic process, when determining the respective measure of similarity. The masking can be a marking out, an omission, an extraction, a non-consideration or a weighting of zero applied to the corresponding at least one sub-image.

A random selection process, as provided in accordance with the present technology, may be advantageous in comparison to a combinatorially complete selection process for masking out the sub-images, since such a combinatorially complete masking out of sub-images, especially if a very large number of sub-images are present, would entail a considerable additional expenditure in terms of time and computation.

It may be irrelevant within the random selection process how high the degree of randomness is or whether, for technical reasons, there is only a so-called pseudo-randomness. The methods according to the present technology can be performed suitably if a random number generator necessary for the selection process is always initialized in the same way or with the same number, the so-called "seed," with which a random number generator is initialized.

The present technology provides that the number of individual registrations can run in series and/or parallel to one another. Running the individual registrations in parallel may generate a time advantage due to a simultaneous execution of multiple individual registrations. Preferably, the individual registrations are thus independent of one another and can take place without knowledge of the optimization steps running in the respective other individual registrations or their resulting similarity measures.

The sub-images which have a scene change during the individual registration may be identified and/or masked out.

For example, those sub-images which do not have a corresponding sub-image in the respective other medical image data set can be masked out.

After identifying the sub-images that have a scene change, a final registration between the first and the second medical image data set may be performed, for example, by masking out the identified sub-images having scene changes, and/or by masking out a sub-image combination used in the individual registrations. By masking out the identified scene changes, this final registration will generally have a higher degree of similarity and thus a more accurate registration than would be the case without such masking.

In embodiments of the methods according to the present technology, the medical image data sets to be registered with one another can also be three-dimensional (3D) or volume images, so that even such image data sets can be registered with one another.

In some embodiments, the first and the second medical image data set for volume images can each be subdivided into n×m×p sub-images, this subdivision also including the condition that at least two of the three parameters can be equated.

Some embodiments can also provide that both medical image data sets represent two-dimensional images, such as projection and/or sectional images, wherein a sectional image can also be a two-dimensional image from a volume image. If two-dimensional medical image data sets are present, the first and second medical image data sets can each be subdivided into n×m sub-images, this also including the possibility that n=m.

In some embodiments, completely different or only partially different sub-images can be masked out randomly for the individual registrations. In the case of a randomly completely different masking out between, for example, two individual registrations, a set of sub-images can be masked out in a respective individual registration and, in subsequent or parallel individual registrations, a set of sub-images which were not contained in the set of masked-out sub-images of the preceding or parallel individual registrations can be masked out at random. In the case of a randomly only partially different masking of sub-images between two individual registrations, a set of sub-images can be masked out in an individual registration, and a set of sub-images can be masked out in subsequent or parallel individual registrations which contains at least one sub-image from the set of the previous or parallel masked-out sub-images of the previous individual registrations.

In some embodiments of the methods according to the present technology, the sub-images can be weighted in the determination of the similarity measures by using an information content, such as variance, standard deviation, or entropy of the intensity or pixel values, that is determined within the corresponding sub-images. This makes it possible to take little or no account of sub-images with little information content, for example largely homogeneous sub-images, when calculating the individual registrations, (e.g., to mask out such sub-images).

Some embodiments of the methods according to the present technology make it possible that, in the process of identifying sub-images having a scene change, a ranking of the similarity measures optimized during the individual registrations can first be produced. A set of the N best similarity measures, and thus a set of the N best individual registrations, can then be determined by means of the ranking. To create a frequency distribution, it is subsequently possible to calculate the number of times the individual sub-images have been masked out across the N best registrations. It is highly probable that sub-images which have been masked out particularly frequently contain a scene change, in particular since their masking out has improved the respective individual registrations. On the basis of this frequency distribution, it is thus possible to identify those sub-images whose frequency exceeds a threshold value, which can be defined in an organ program, for example. Sub-images whose frequency exceeds the threshold value can be identified as those sub-images which have a scene change, since they particularly frequently lead to an improved individual registration.

Further embodiments of the methods according to the present technology make it possible for the sub-images to be further subdivided into sub-sub-images. In some advantageous embodiments, this can be done by repeating the subdivision, individual registration, scene change identification, and final registration steps, wherein only the sub-images for which a scene change was determined in the previous pass are permitted for the repetition. These sub-images can then be subdivided into more finely resolved sub-sub-images in order to more precisely delimit the scene change, for example an introduced foreign object. Such repetition can also be carried out multiple times until, for example, the sub-sub-images correspond to individual pixels and the scene change has thus been segmented with the highest possible resolution. The methods according to the present technology can do this in particular if the area of the sub-images that exceed a threshold value for the frequency occupies an excessively large image area. An advantage of this sub-subdivision can be that a finer subdivision makes it possible to detect smaller scene changes, for example smaller foreign objects, more accurately in order to achieve a higher accuracy of the final registration.

Further example configurations can also provide that a sub-similarity measure is determined for each sub-image and that the similarity measures for the individual registrations are aggregated from these sub-similarity measures of non-masked sub-images. An advantage of these embodiments can be that the present technology can combine the previously calculated sub-similarity measures and discard a subset of sub-similarity measures much more quickly than performing a complete image re-registration with the omitted sub-images.

The present technology further provides devices such as an X-ray device, in particular a C-arm X-ray device, for example a mobile C-arm X-ray device, a computer tomograph, in particular a cone beam computer tomograph, and gantry-based systems which produce recordings of image data sets by means of X-rays. The devices according to the present technology can include an image processing unit with a memory unit on which instructions are stored which, when executed by a computing unit, bring about a method according to any of the embodiments of present technology.

A largely software-based implementation of the method has the advantage that even previously used registration methods for image recording systems can be retrofitted in a simple manner by a software update in order to operate according to the present technology. The problem disclosed herein may also be solved by a corresponding computer program product having a computer program which can be loaded directly into a memory device of an image recording system, for example a mobile C-arm, said program having program sections for executing all the steps of the method according to the present technology when the computer program is executed in the control device. In addition to the computer program, such a computer program product may optionally comprise additional components such as documentation and/or additional components, including hardware components for using the software.

A computer-readable medium, for example a memory stick, a hard disk or another portable or permanently installed data carrier, on which the program sections of the computer program which can be read in and executed by a computer unit of the control device are stored, can be used for transport to the control device and/or for storage on or in the control device. A connection to a hospital information system connected to a network, to a radiology information system or to a global network, in which systems are stored the program sections of the computer program which can be read in and executed by a computer unit of the control device, can also be used for the transport. The computer unit, and/or any of the other units disclosed herein such as an image output unit, an input unit, and/or an image processing unit, can have, for example, one or more cooperating microprocessors or the like for this purpose, each of which may be in communication with one or more non-transitory computer-readable media having computer-executable instructions stored thereon for execution of the corresponding unit functions.

Certain embodiments of the present technology will now be explained in more detail with reference to the figures.

Figure 1A:
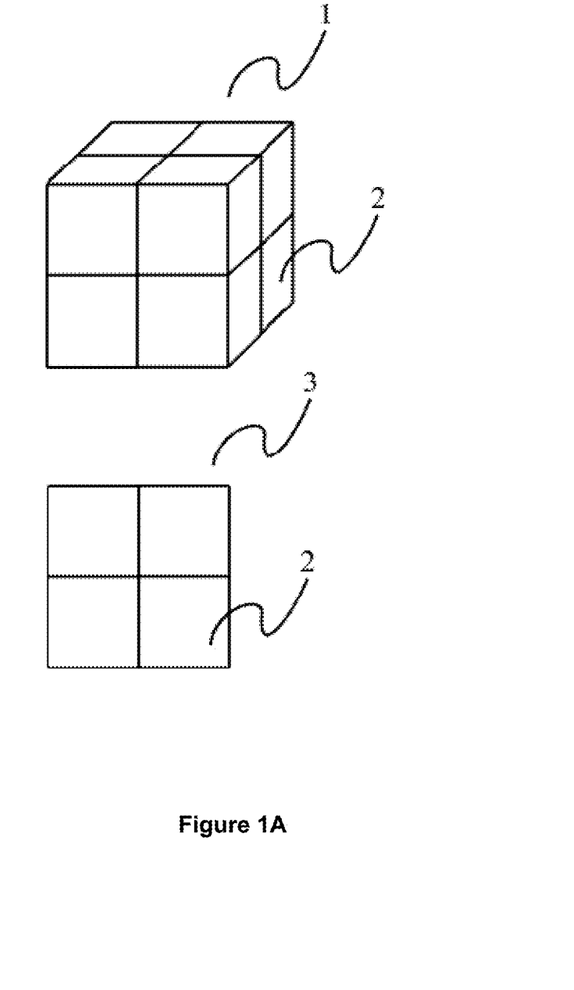
FIGS. 1A and 1B schematically show two-dimensional and three-dimensional image data sets which can be utilized by the methods of the present technology.

FIG. 1A schematically shows a three-dimensional image data set 1 which is subdivided into its 2×2×2 sub-images 2. Furthermore, FIG. 1A also shows a two-dimensional image data set 3 which is subdivided into 2×2 sub-images 2.

Figure 1B:
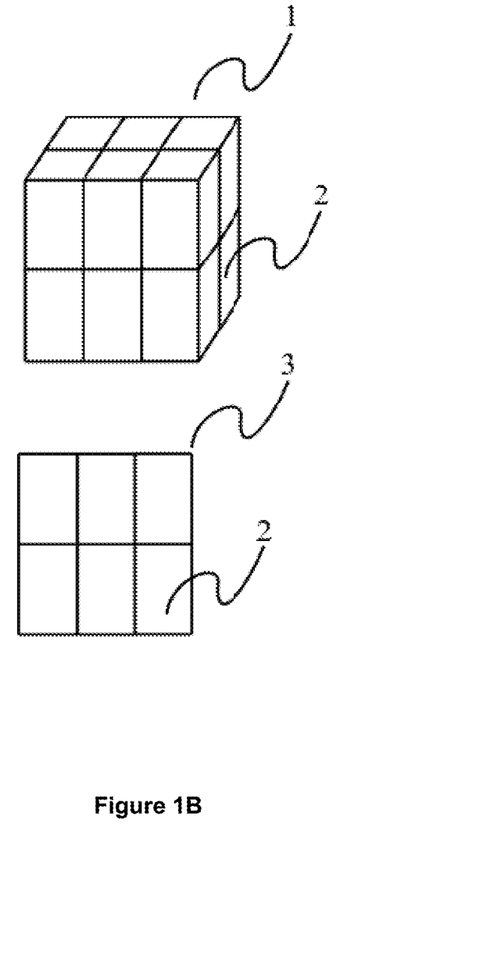

FIG. 1B schematically shows a three-dimensional image data set 4 which is subdivided into its 2×2×3 sub-images 2. Furthermore, FIG. 1B also shows a two-dimensional image data set 2 which is subdivided into 2×2 sub-images 2.

Figure 2A:
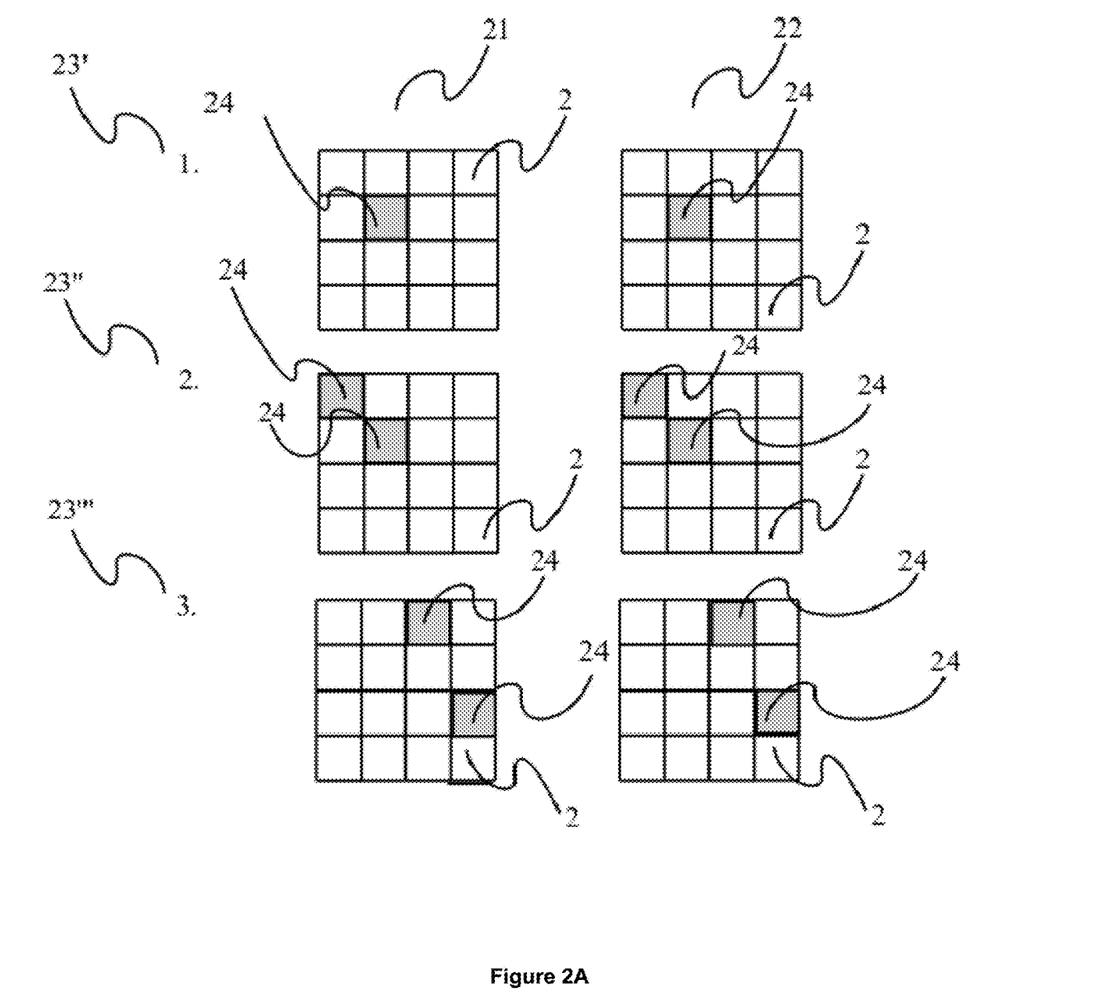
FIG. 2A schematically shows the process of stochastic masking.

FIG. 2A schematically shows an example process of stochastically masking out at least one two-dimensional sub-image 2 via a plurality of individual registrations (23', 23", 23''') between a first image data set 21 and a second image data set 22. For an individual registration 23', a sub-image 24 is masked out in both two-dimensional image data sets (21, 22) and a measure of similarity between the two image data sets (21, 22) is determined. The methods according to the present technology can now determine a new measure of similarity in a further, second, individual registration 23", two sub-images 24 now being masked out in both image data sets (21, 22), wherein one of the two sub-images 24 is also masked out in a first individual registration 23' and thus does not have to be taken into account for determining the measure of similarity in a second individual registration 23", since the individual registrations (23', 23", 23''') are independent of one another. In a further individual registration, the third individual registration 23''', different sub-images 24 are masked out than in the first and second individual registrations (23', 23"), which in certain cases also do not correspond to the sub-images 24 masked out in the previous individual registrations. FIG. 2A thus represents the aforementioned stochastic selection of the sub-images 24 to be masked out for each individual registration.

Figure 2B:
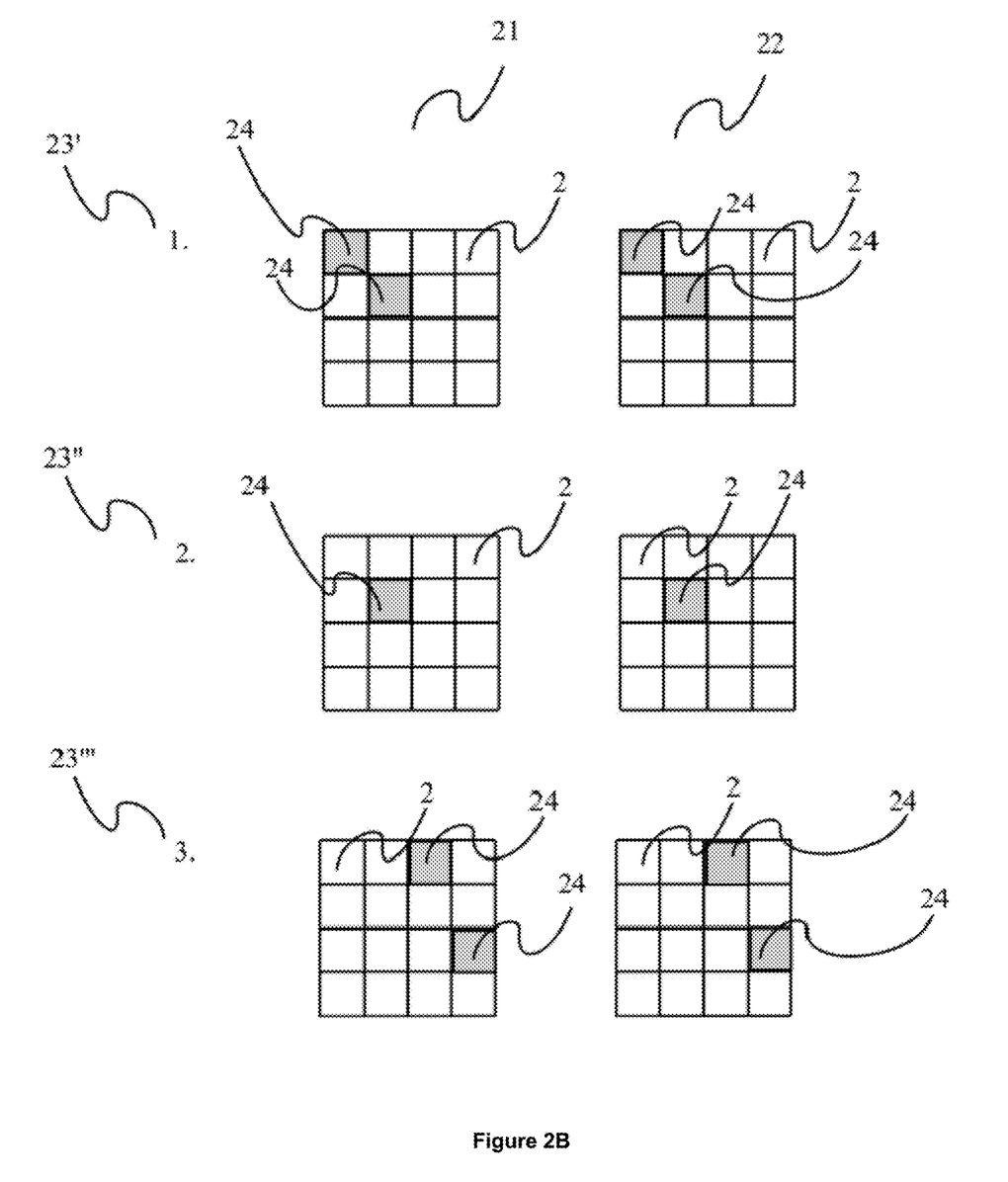
FIG. 2B schematically illustrates the process of stochastic masking in an alternate order of possible individual registrations.

The variant of the order of individual registrations shown in FIG. 2A shows only one sequence as an example. FIG. 2B likewise shows the possible maskings of sub-images 24 during the individual registrations of FIG. 2A, in a different order. From this order of the individual registration it can be seen that several sub-images 24 can be masked out already in the first individual registration 23' and, in the subsequent individual registrations 23" and 23''', fewer, more, and/or a subset of the sub-images masked out in the first registration 23' can be masked out. The possible method sequences shown in FIGS. 2A and 2B result from the property of the stochastic masking of the present technology and are thus generally random. In this case, the number of sub-images 24 to be masked out can be constant over all the individual registrations and only the location of the sub-images 24 to be masked out can be selected stochastically or randomly. It is also possible, however, to additionally vary the number of sub-images 24 to be masked out stochastically or randomly over the individual registrations.

Figure 2C:
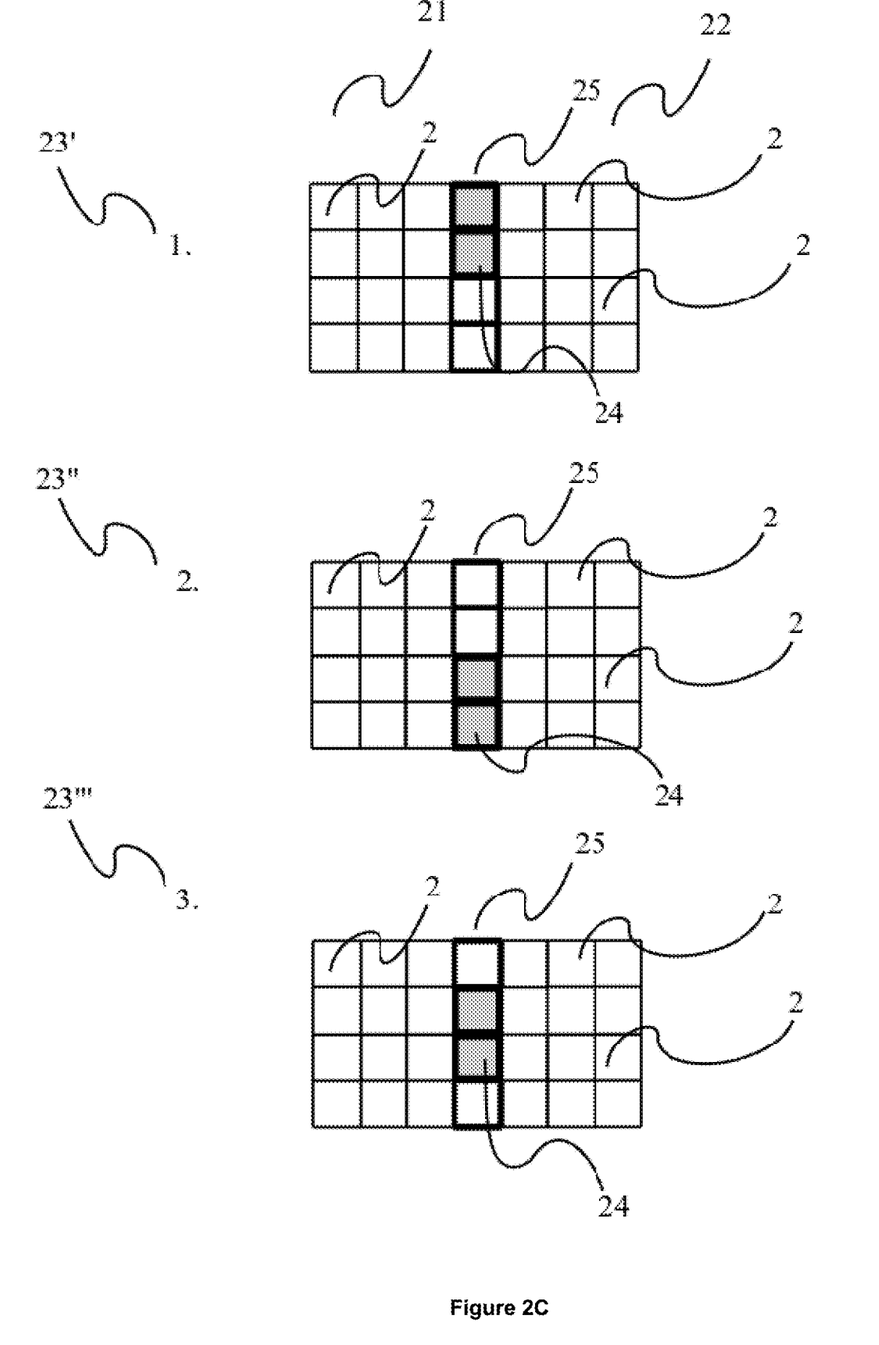
FIG. 2C schematically illustrates the process of stochastic masking in an overlapping area between two medical image data sets FIG. 3 discloses a frequency diagram of a two-dimensional image data set.

The situation illustrated in FIG. 2C represents an embodiment in which the pixel coordinates of the sub-images 2 coincide in both image data sets. In further embodiments, it is possible for the pixel coordinates to be located at different locations of the two medical image data sets. This is advantageous, for example, if the purpose of the registration is to produce a large-format image, for example a panoramic image, and the two image data sets (21, 22) have overlaps 25 only at their edges. For example, the right image edge of the first image data set 21 may have a correspondence at the left image edge of the second image data set 22. In such an embodiment, it is therefore particularly advantageous to select the sub-images 24 to be masked out only in the overlap region 25 of the two medical image data sets (21, 22), with the result that their position in the first image data set 21 would be selected at the right-hand edge, but in the second image data set 22 would be selected at the left-hand edge of the image.

Figure 3:
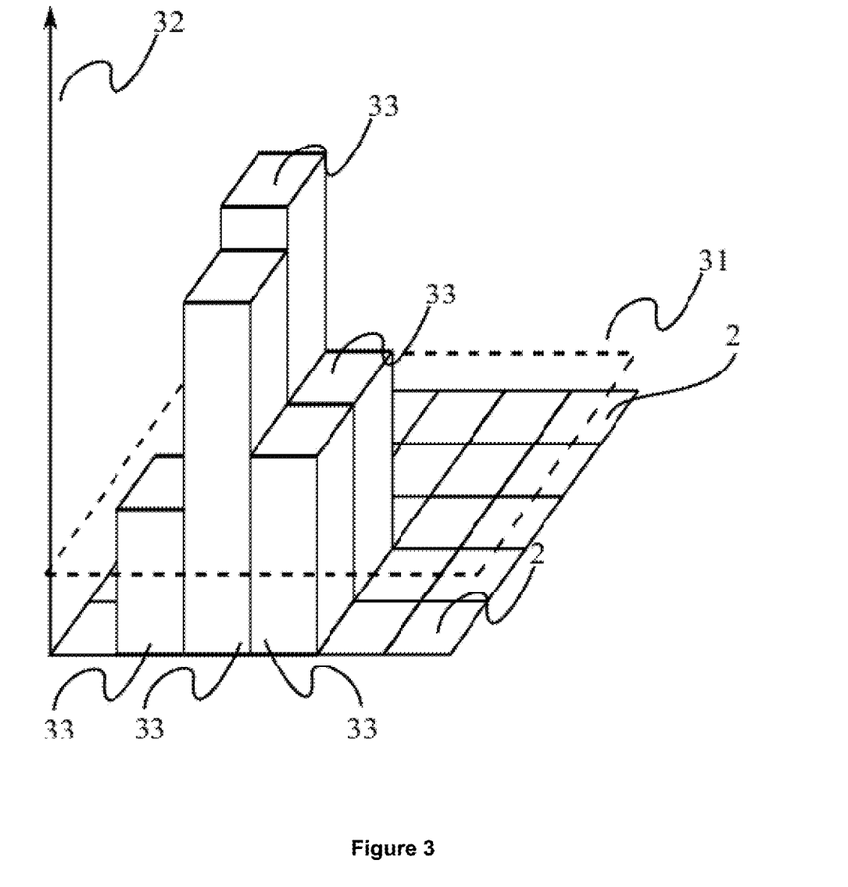

FIG. 3 discloses a frequency diagram of a two-dimensional image data set 3 which has been subdivided into sub-images 2, the frequency 32 representing a measure of the most frequently masked sub-images 33. As has already been disclosed above, the methods according to the present technology make it possible for a ranking of the similarity measures determined by the individual registrations to be initially produced in the scene change identification step. A set of the best similarity measures can then be determined by means of the ranking, and the sub-images 2 which are masked out for the calculation of the best similarity measures can likewise be determined. The masked-out sub-images 33 for which the frequency 32 exceeds a threshold value 31 that can be defined in an organ program, for example, can then be identified from the set of defined sub-images 2. Sub-images 2 whose frequency 32 exceeds the threshold value 31 can be identified as the sub-images 33 which have a scene change.

Figure 4:
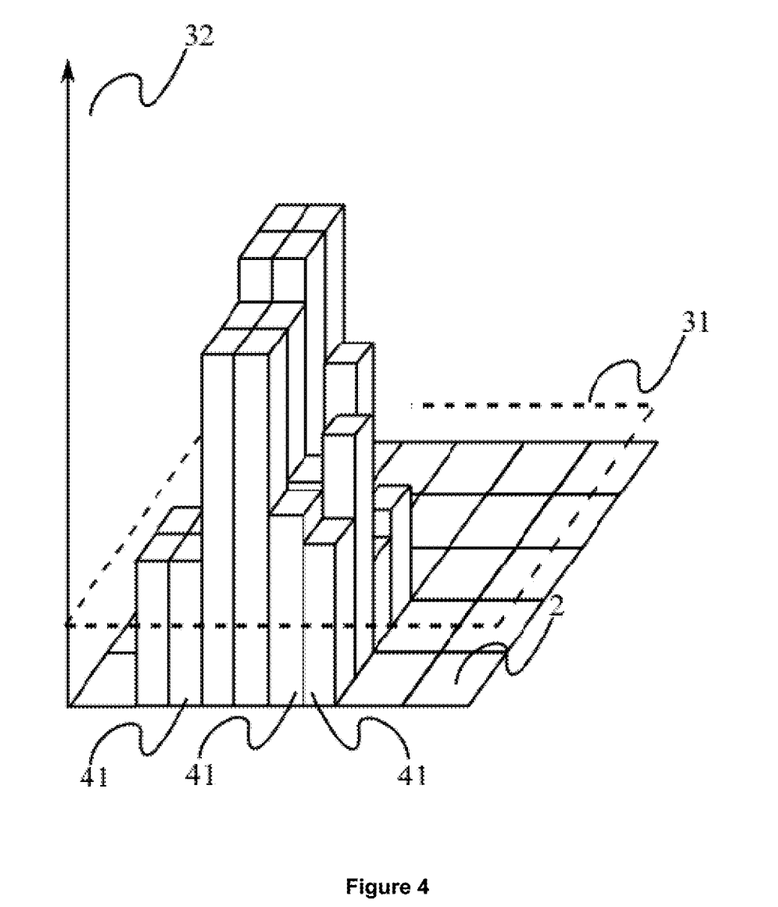
FIG. 4 schematically shows the subdivision of sub-images into sub-sub-images.

FIG. 4 shows that the methods according to the present technology make it possible for the sub-images 2 to be further subdivided into sub-sub-images 41. This can take place, for example, as described above, by one or more repeated executions of portions of the registration methods, for example if a number of individual registrations predetermined in an organ program is exceeded and/or a similarity measure likewise predetermined in an organ program is not achieved, or after the performance of the final registration, for example in order to achieve a higher-quality similarity measure of the final registration. The subdivision of sub-images 2 into sub-sub-images 41 can be carried out, for example, if the area of the sub-images 2 which exceed a threshold value 31 for the frequency 32 exceeds a predetermined limit value for this area. The limit value for this area can likewise be set in a corresponding organ program. An advantage of this this aspect of the present technology can be that a finer subdivision of sub-images 2 into sub-sub-images 41 makes it possible to detect smaller scene changes, for example smaller foreign objects, correctly and therefore have more sub-images 2 and/or sub-sub-images 41 available for subsequent individual registrations and thus be able to determine a higher-quality similarity measure.

Figure 5:
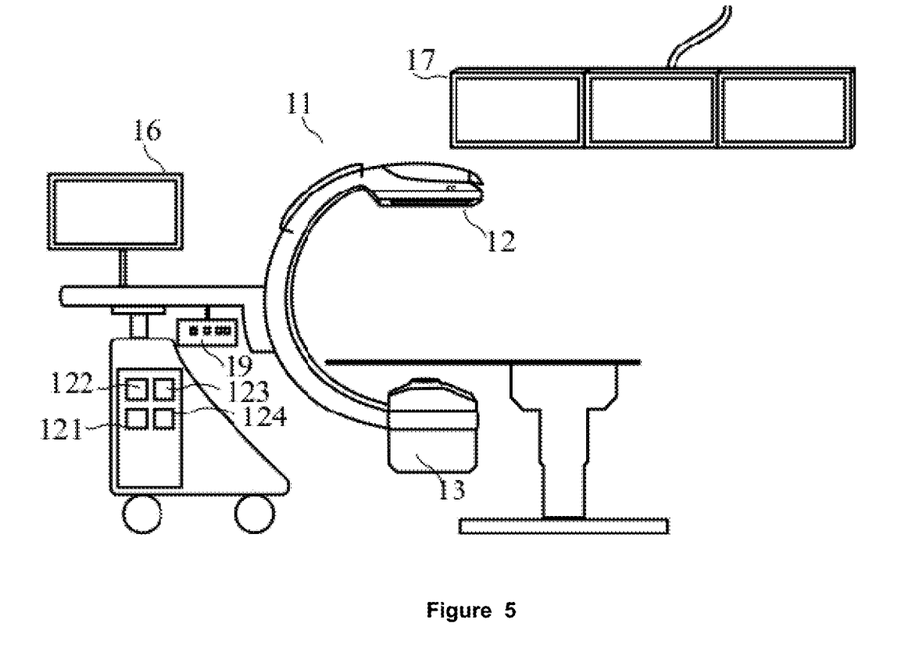
FIG. 5 shows a device according to the present technology in the form of a mobile C-arm.

FIG. 5 schematically shows a device according to the present technology designed as a mobile C-arm 11 that is provided for the implementation of the methods according to the present technology.

The C-arm 11 carries an X-ray generator 13 at one end and an X-ray image detector 12, such as a flat detector or an image amplifier, at the other end and opposite the X-ray generator 13. The C-arm 11 can be adjusted under the control of a motor in a plurality of axes in space, the axes having sensors for detecting the extent of the adjustment.

The device further comprises an image-processing unit 121, a memory unit 122, a control unit 123 and a network interface 124. By means of the network interface 124, data, such as image data sets and results of the methods according to the present technology, can be distributed or made available in a network.

The image processing unit 121 comprises a control unit 122, on which the two- or three-dimensional image data sets used for the methods according to the present technology can be stored or loaded. These image data sets can either be loaded from a server or recorded by means of the C-arm 11 before or during an intervention. The memory unit further comprises instructions which are used for carrying out the methods according to the present technology by means of a computing unit.

Furthermore, the device can contain a GUI, having an image output unit (16, 17) and an input unit 19, with which corresponding settings can be made for the image processing unit 121 in corresponding organ programs.

LIST OF REFERENCE NUMBERS

1 Three-dimensional data set
2 Sub-image
3 Two-dimensional image data set
11 C-arm
12 X-ray image detector
13 X-ray generator
16, 17 Image output unit
19 Input unit
121 Image processing unit
122 Memory unit
123 Computing unit
124 Network interface
21 First image data set
22 Second image data set
23' First individual registration
23" Second individual registration
23'" Third individual registration
24 Masked-out sub-image
25 Overlap area of sub-images
31 Threshold criterion
32 Frequency scale
33 Masked-out sub-images
41 Sub-sub-images

What is claimed is:

1. A method of registering two sets of medical image data taking into account scene changes, the method comprising, under control of one or more processors:
   a. receiving a first medical image data set and a second medical image data set from one or more medical devices;
   b. subdividing each of the first and second medical image data sets into an equal number of sub-images;

c. performing a plurality of individual registrations between the first and second medical image data sets with respective optimization of a similarity measure, wherein, for each individual registration, at least one sub-image of the first and/or second medical image data set is masked out by means of a random process when determining the respective similarity measure;

d. identifying the sub-images that have a scene change; and e. performing a final registration between the first medical image data set and the second medical image data set by masking out the sub-images identified in step d or a masked-out sub-image combination used in step c.

2. The method of claim 1, wherein both medical image data sets are three-dimensional volume images.

3. The method of claim 2, wherein the first medical image data set and the second medical image data set are each subdivided into n×m×p sub-images.

4. The method of claim 1, wherein both medical image data sets are two-dimensional images, preferably at least one of projection images or sectional images.

5. The method of claim 4, wherein the first medical image data set and the second medical image data set are each subdivided into n×m sub-images.

6. The method of claim 1, wherein at least two sub-images are masked out for steps d and e, and wherein completely different or only partially different sub-images are masked out for each registration of step c.

7. The method of claim 6, wherein, when determining the respective similarity measure, the sub-images are weighted with an information content determined within the corresponding sub-images.

8. The method of claim 1, wherein identifying the sub-images that have a scene change comprises:
creating a ranking of the determined similarity measures;
determining a set of best similarity measures based on the created ranking and determining the masked-out sub-images in the calculation thereof; and
identifying the specific sub-images whose frequency exceeds a threshold value as the sub-images which have a scene change.

9. The method of claim 1, further comprising subdividing the sub-images into sub-sub-images.

10. The method of claim 1, further comprising determining a sub-similarity measure for each non-masked sub-image, and wherein the determined similarity measures are aggregated from the sub-similarity measures.

11. The method of claim 1, wherein the at least one sub-image to be masked out is selected pseudo-randomly for each individual registration.

12. An X-ray device comprising an image processing unit having a memory unit storing instructions that, when executed, cause one or more processors of the image processing unit to execute the method of claim 1.

13. A tangible, non-transitory computer-readable storage medium having stored thereon a computer program which can be loaded directly into a memory unit of a control unit of an X-ray device, in particular a C-arm X-ray device, having program sections in order to execute the method of claim 1.

14. A tangible, non-transitory computer-readable storage medium having stored thereon program sections which can be read and executed by a computer unit to execute the method of claim 1.

* * * * *